United States Patent
Kang

(10) Patent No.: US 8,136,189 B2
(45) Date of Patent: Mar. 20, 2012

(54) METHOD FOR CONTROLLING WASHING COURSE OF WASHING MACHINE

(75) Inventor: Dong Won Kang, Changwon-si (KR)

(73) Assignee: LG Electronics Inc., Seoul (KR)

( * ) Notice: Subject to any disclaimer, the term of this patent is extended or adjusted under 35 U.S.C. 154(b) by 596 days.

(21) Appl. No.: 11/630,992

(22) PCT Filed: Feb. 28, 2006

(86) PCT No.: PCT/KR2006/000683
§ 371 (c)(1),
(2), (4) Date: Jun. 2, 2009

(87) PCT Pub. No.: WO2006/091055
PCT Pub. Date: Aug. 31, 2006

(65) Prior Publication Data
US 2009/0229058 A1    Sep. 17, 2009

(30) Foreign Application Priority Data
Feb. 28, 2005  (KR) .......................... 10-2005-0017022

(51) Int. Cl.
*D06F 33/00* (2006.01)
*B08B 7/04* (2006.01)
*B08B 3/04* (2006.01)
*B08B 3/06* (2006.01)

(52) U.S. Cl. ............... 8/159; 134/18; 134/19; 134/25.4; 134/33; 68/12.12

(58) Field of Classification Search ............... 8/158, 159; 68/12.12; 134/19, 25.4, 18
See application file for complete search history.

(56) References Cited

U.S. PATENT DOCUMENTS

| | | | |
|---|---|---|---|
| 4,711,103 A * | 12/1987 | Mori et al. | 68/12.05 |
| 2002/0032932 A1 * | 3/2002 | Kim et al. | 8/158 |
| 2003/0051296 A1 | 3/2003 | Broker et al. | |
| 2003/0184597 A1 | 10/2003 | Jo et al. | |
| 2004/0231708 A1 | 11/2004 | Kim et al. | 134/34 |
| 2007/0130698 A1 * | 6/2007 | Kim | 8/158 |

FOREIGN PATENT DOCUMENTS

| | | | |
|---|---|---|---|
| CN | 1446279 A | | 10/2003 |
| JP | 02289298 A | * | 11/1990 |
| KR | 10-0175231 B1 | | 5/1999 |
| KR | 10-2005-0004616 A | | 1/2005 |

OTHER PUBLICATIONS

JP 02-289298, Nakajima et al.; Nov. 29, 1990; English translation of abstract.*
Korean Office Action dated Jun. 30, 2011 issued in Application No. 10-2005-0017022.
European Search Report dated May 23, 2011 issued in Application No. 06 71 6133.

* cited by examiner

*Primary Examiner* — Michael Kornakov
*Assistant Examiner* — Natasha Campbell
(74) *Attorney, Agent, or Firm* — KED & Associates LLP

(57) ABSTRACT

A method for controlling operation of a washing machine is provided. The method may include performing heated washing courses at different temperatures while also selectively controlling an operating rate of a driving motor to enhance sterilizing effects on items being washed while protecting against damage to the items being washed. Performing these heated washing courses may include selecting an infant clothes oriented washing program from a plurality of washing programs, and performing a washing operation in accordance with one of a plurality of operating modes associated with the selected infant clothes oriented washing program, including controlling at least one of a washing course temperature or an operating rate of a driving motor of the washing machine.

6 Claims, 3 Drawing Sheets

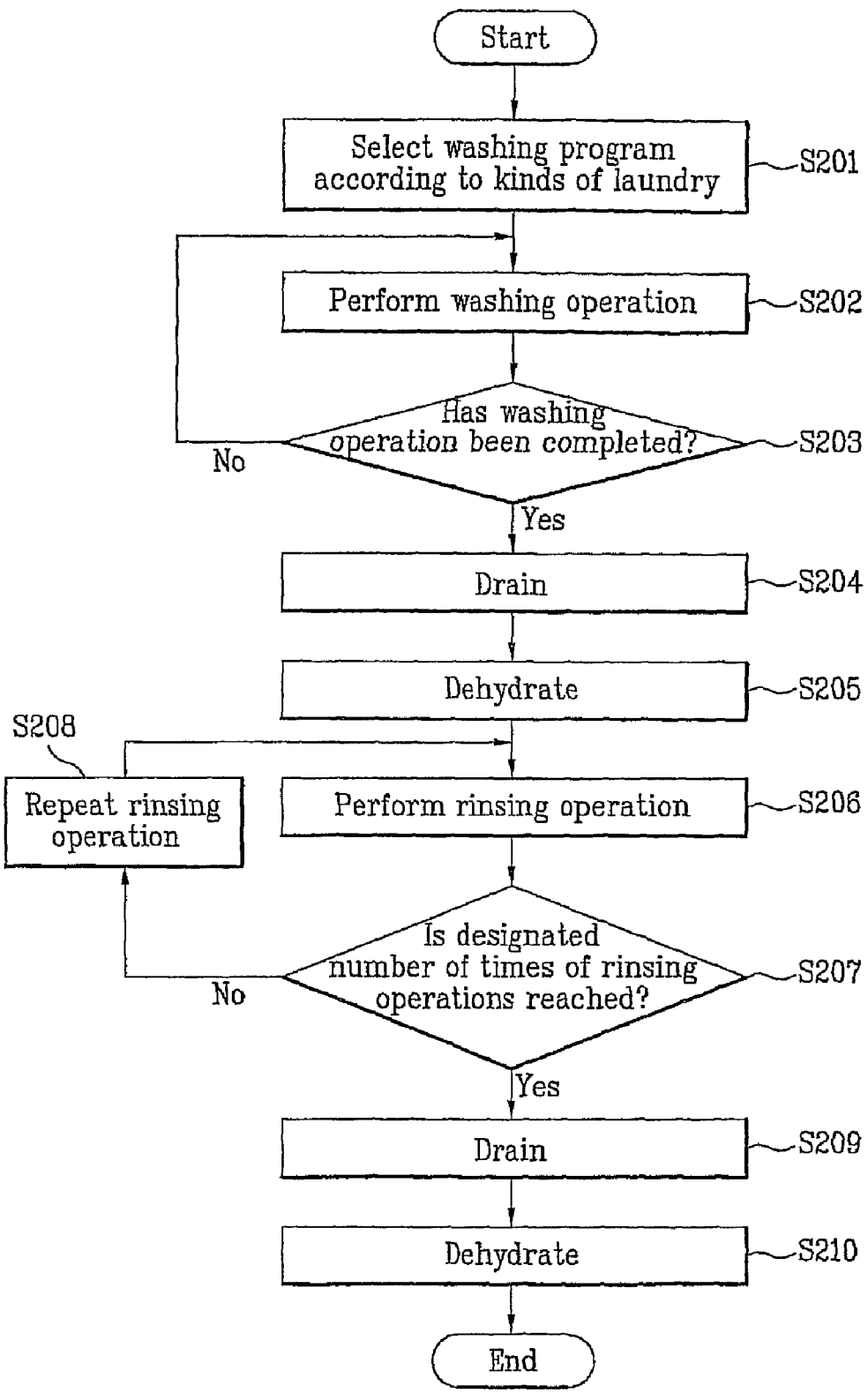

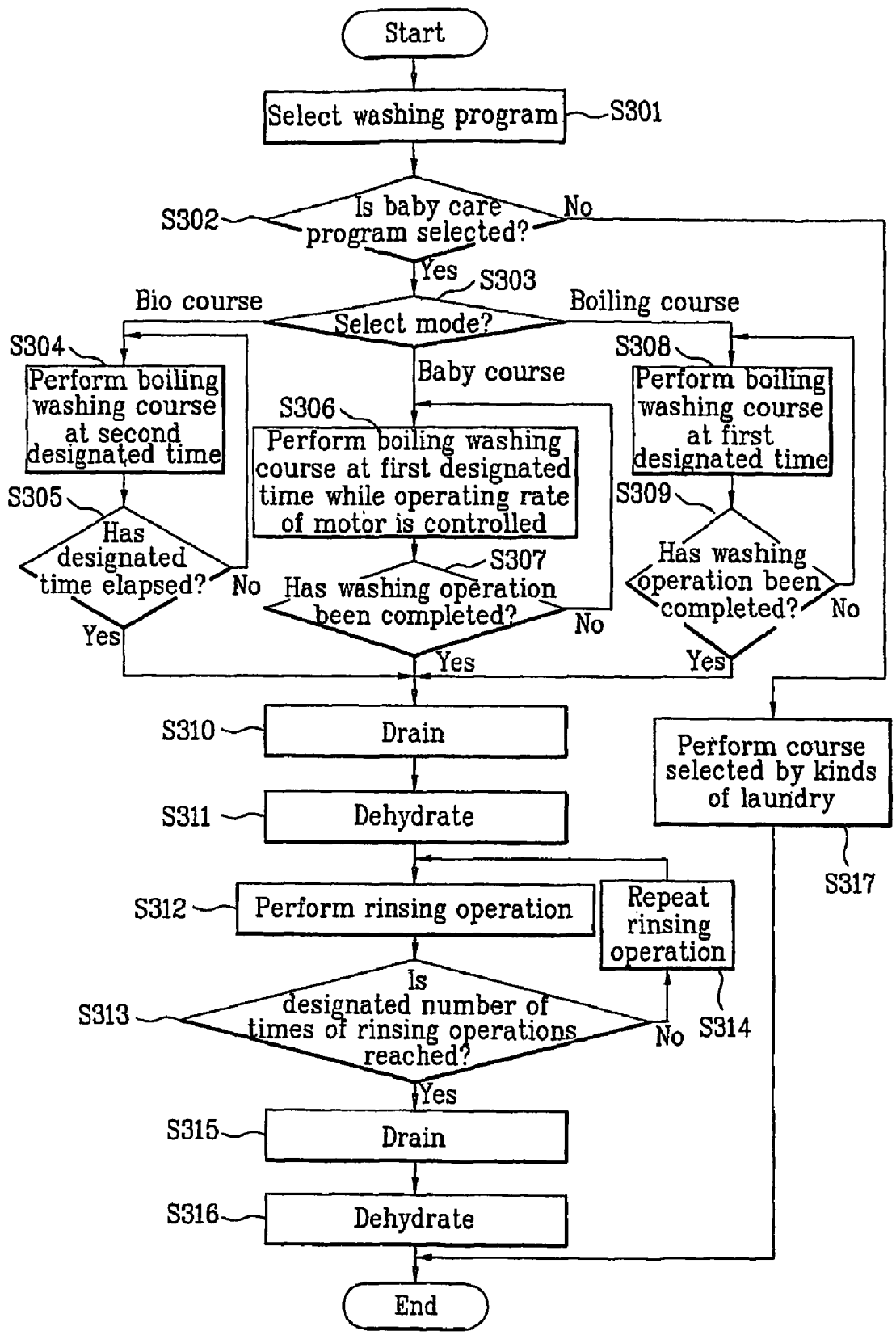

METHOD FOR CONTROLLING WASHING COURSE OF WASHING MACHINE

TECHNICAL FIELD

The present invention relates to a washing machine, and more particularly, to a method for controlling a washing operation of a washing machine, to which boiling washing courses performed at different temperatures and having a controlled operating rate are selectively applied to increase protecting and sterilizing effects of clothes for infants.

BACKGROUND ART

Generally, a washing machine removes dust from laundry using chemical reaction of a detergent dissolved in washing water and friction between the washing water and the laundry due to rotating hydraulic power of the washing water generated by mechanical reaction, and selectively perform washing, rinsing, and dehydrating operations.

The above washing machine washes the laundry using one of various programs selected by a user.

Hereinafter, with reference to FIGS. 1 and 2, a washing operation of a conventional washing machine will be described in detail.

FIG. 1 is a block diagram of a general washing machine, and FIG. 2 is a flow chart illustrating a conventional method for controlling a washing operation of a washing machine.

As shown in FIGS. 1 and 2, a conventional washing machine comprises an input unit 11 for allowing a user to input a control signal for controlling operations of the washing machine, a controller 12 for controlling the overall operation of the washing machine according to an output signal of the input unit 11, a water supply valve driving unit 16 for operating water supply valves, such as a cold water valve, a hot water valve, and a shower valve, under the control of the controller 12, a drain valve driving unit 17 for operating a drain valve so that washing water supplied through the water supply valve driving unit 16 is drained, a water level sensing unit 14 for sensing a water level in a tub, a rotational speed sensing unit 15 for sensing a rotational speed of the tub, a motor driving unit 13 for operating a motor to perform a washing operation according to a control signal of the controller 12, and a heating unit (not shown) for heating or drying the washing water.

The operation of the above washing machine is controlled as described below.

As shown in FIG. 2, a washing program is selected according to kinds of laundry, such as cotton, synthetic fiber, and delicate material (S201).

Then, when a start key is inputted, a washing operation is performed according to a set washing course based on the selected program (S202). After the washing operation is completed (S203), dirty washing water resulting from the washing operation is drained to the outside of the washing machine (S204).

The laundry is intermittently dehydrated for a designated time. After the intermittent dehydrating of the laundry is completed, the laundry is dehydrated at a rotational speed differing from that of the intermittent dehydrating of the laundry for a designated time (S205).

After the dehydrating of the laundry is completed, a rinsing operation including supplying water, rinsing, and draining, is performed (S206).

Generally, the rinsing operations are repeated a designated number of times. After one rinsing operation is finished, it is determined whether or not the designated number of times of the rinsing operations have been performed (S207). When it is determined that the designated number of times of the rinsing operations have not been yet performed, another rinsing operation is performed (S208).

When it is determined that the designated number of times of the rinsing operations have been performed, the washing water is drained (S209), and the laundry is dehydrated (S210).

The above washing process is performed based on the set program. The washing process may be performed by other methods.

The above washing course and selection of the washing course of the conventional washing machine have several problems, as described below.

In the conventional washing machine, the selection of the washing course by a user is simply performed according to kinds of laundry without consideration of an individual using the laundry or a use of the laundry, thus being limited.

Currently, the increase of infant dermatitis, such as atopic dermatitis, due to the increase of environmental pollution has become an issue. The above selection of the simple washing course cannot effectively cope with this problem.

Particularly, clothes for infants need to be frequently washed due to growth characteristics of the infants. However, the above washing process does not consider the protection of the clothes for infants.

In order to increase a rinsing capacity of laundry during the rinsing operation, an additional rinsing operation selected by a user is performed. Here, the additional rinsing operation is limited in a rinsing effect, in which washing water not containing a detergent is supplied to the laundry to rinse detergent components and other contaminants out of the laundry.

The remaining of the detergent components and the other contaminants in the laundry easily affects weak skin of infants, thereby deteriorating user's reliability to the washing machine.

DISCLOSURE OF INVENTION

Technical Problem

An object of the present invention devised to dissolve the problem lies on a method for controlling a washing operation of a washing machine, to which boiling washing courses performed at different temperatures and having a controlled operating rate are selectively applied to increase protecting and sterilizing effects of clothes for infants.

Technical Solution

The object of the present invention can be achieved by providing a method for controlling a washing operation of a washing machine comprising forming a washing program comprising an infant clothes-oriented program; selecting the infant clothes-oriented program from the washing program; and performing the washing operation according to an operating mode of the infant clothes-oriented program, when the infant clothes-oriented program is selected.

In another aspect of the present invention, provided herein is a method for controlling a washing operation of a washing machine comprising selecting one of an infant clothes-oriented program and washing courses, set according to kinds of laundry to be washed, from a washing program; and performing the washing operation by controlling the operating rate of a motor and a temperature of the washing operation according to a corresponding operating mode of the infant clothes-oriented program, when the infant clothes-oriented program is selected.

The infant clothes-oriented program comprises an operating mode for removing protein contaminants from infant clothes to be washed, and, in the operating mode for removing the protein contaminants from the infant clothes, a boiling washing course at a temperature of 40° C. is performed for 20 minutes.

The infant clothes-oriented program comprises an operating mode for sterilizing and disinfecting infant clothes to be washed and preventing damage to the infant clothes, and, in the operating mode for sterilizing and disinfecting the infant clothes and preventing the damage to the infant clothes, a boiling washing course is performed under the condition that the operating rate of a motor is controlled so that an ON-time of the motor is shorter than an OFF-time.

The infant clothes-oriented program comprises an operating mode for increasing the sterilizing effect of cotton-made infant clothes to be washed, and, in the operating mode for increasing the sterilizing effect of the cotton-made infant clothes, a boiling washing course without varying the operating rate of a motor is performed.

Preferably, rinsing operations are repeated at different number of times according to the selected operating mode, after the washing operation is completed.

Advantageous Effects

The method of the present invention has effects, as described below.

First washing courses are selected according to kinds of laundry to be washed, and an infant clothes-oriented program for increasing sterilizing and disinfecting effect of infant clothes is selected, thereby satisfying various user requirements.

Second, the operating rate of a motor is controlled when a boiling washing course is performed, thereby allowing the infant clothes, which need to be frequently washed, to be delicately treated.

Third, it is possible to remove protein contaminants, such as blood and chocolate, from the infant clothes, thereby increasing a washing capacity of the washing machine.

BRIEF DESCRIPTION OF THE DRAWINGS

The accompanying drawings, which are included to provide a further understanding of the invention, illustrate embodiments of the invention and together with the description serve to explain the principle of the invention.

In the drawings:

FIG. 2 is a flow chart illustrating a conventional method for controlling a washing operation of a washing machine; and FIG. 3 is a flow chart illustrating a method for controlling a washing operation of a washing machine in accordance with the present invention.

BEST MODE FOR CARRYING OUT THE INVENTION

Figure 1:
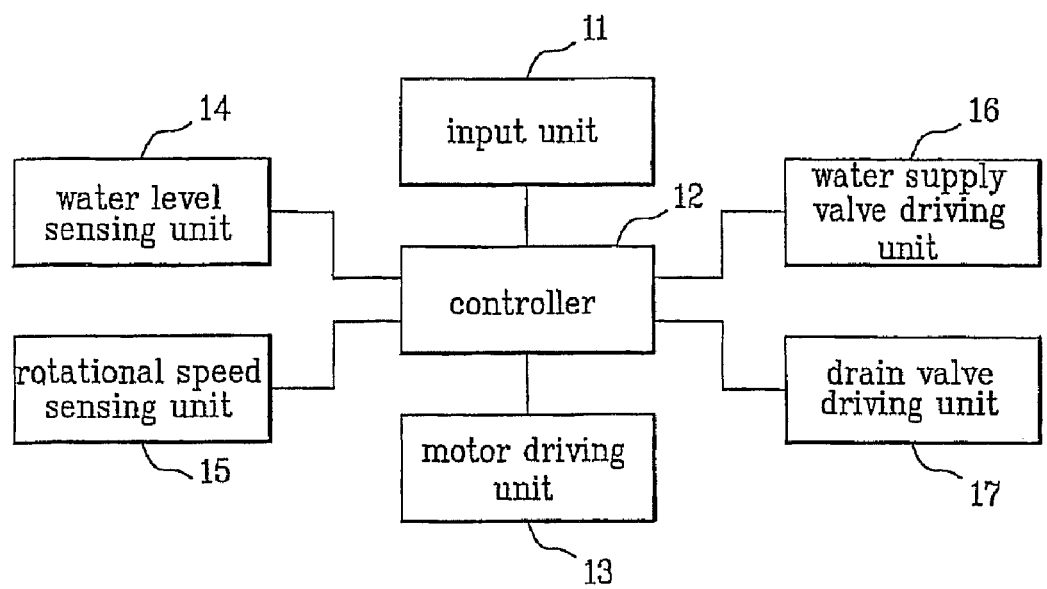
FIG. 1 is a block diagram of a general washing machine.

Reference will now be made in detail to the preferred embodiment of the present invention, examples of which are illustrated in the accompanying drawings.

FIG. 3 is a flow chart illustrating a method for controlling a washing operation of a washing machine in accordance with the present invention.

In the method in accordance with the present invention, a washing course of the washing machine is selected in consideration of the age of an individual using the laundry or the use of the laundry, thereby satisfying various user requirements.

Particularly, infant clothes are not treated by a general washing course, but are treated by a washing course using a separate infant clothes-orientated program (a baby care program), which meets the characteristics of infant clothes.

The baby care program is divided into first, second and third modes. In the first mode (a bio course), in order to eliminate protein contaminants, such as blood and chocolate, from infant clothes, a boiling, or heated washing course at a designated temperature (40° C.) is performed. In the second mode (a baby course), in order to increase the sterilizing effect on infant clothes in view of the characteristics of the infant clothes, a boiling, or heated washing course at a high temperature of more than 95° C. while controlling the operating rate of a driving motor is performed so that the infant clothes, which may be frequently washed, are not damaged. In the third mode (a boiling course), in order to increase the sterilizing effect of cotton-made infant clothes, a boiling, or heated washing course at a temperature of 95° C. is performed. A user can select one out of the first, second, and third modes in consideration of kinds and uses of the clothes. and third modes in consideration of kinds and uses of the clothes.

Specifically, as shown in FIG. 3, after a user selects a washing program (S301) and inputs a start key, it is determined whether or not the washing program selected by the user is the infant clothes-orientated program (the baby care program) (S302).

When the user selects the washing program, the selection of a general washing course according to kinds of laundry is distinguished from the selection of a washing course based on the infant clothes-orientated program.

When the user does not select the infant clothes-oriented program, but selects a washing course according to kinds of the laundry, such as cotton, synthetic fiber, or delicate material (underwear), a washing operation according to the corresponding washing course is performed (S317).

On the other hand, when the user selects the infant clothes-orientated program, the user selects one mode of the infant clothes-orientated program (S303).

In this embodiment, the infant clothes-oriented program is divided into the first mode for removing protein from the laundry, the second mode for sterilizing the laundry and preventing the laundry from being damaged, and the third mode for sterilizing the laundry.

However, in addition to the above modes, other modes according to the characteristics of the infant clothes may be dependently or simultaneously added to the infant clothes-oriented program.

When the washing mode selected by the user is the first mode (the bio course), a boiling washing course at a second designated temperature for removing protein contaminants, such as blood or chocolate, from the laundry is performed (S304).

Here, the second designated temperature is set in the range of 38-42° C. Preferably, the second designated temperature is set to 40° C., which is the most effective to remove the protein contaminants from the laundry.

The boiling washing course at the above temperature is performed for a designated time. Preferably, the designated time is set to 20 minutes (S305).

The user selects the first mode so as to remove protein contaminants, which cannot be removed from laundry by a general washing operation, from the laundry.

When the washing mode selected by the user is the second mode (the baby course), a boiling washing course at a first designated temperature (the highest water temperature in the washing machine), for example, 95° C., in consideration of the characteristics of infant clothes, such as frequent washing of the infant clothes for sterilization and disinfection, is performed (S306), while the operating rate of a motor is controlled so that an ON-time of the motor is short and an OFF-time of the motor is long.

The washing operation set to the above condition is completed (S307).

When the washing mode selected by the user is the third mode (the boiling course), a boiling washing course at the first designated temperature (the highest water temperature in the washing machine) for maximally increasing the sterilizing effect of laundry made of cotton is performed (S308).

The washing operation set to the above condition is completed (S309).

After the washing operation according to the washing mode selected by the user is completed, dirty washing water resulting from the washing operation is drained (S310).

Thereafter, the laundry is intermittently dehydrated for a designated time, and, after the intermittent dehydration is completed, the laundry is dehydrated at a rotational speed differing from that of the intermittent dehydration for a designated time (S311).

After the dehydration is completed, a rinsing operation including supplying water, rinsing, and draining is performed (S312).

In general, the rinsing operations are repeated a designated number of times. After one rinsing operation is completed, it is determined whether or not the designated number of times of the rinsing operations have been performed (S313), and the rinsing operations are repeated until the designated number of times is reached according to the determined result (S314).

When the rinsing operation has been repeated the designated number of times, the washing water in the washing machine is drained (S315), and the laundry is dehydrated (S316).

Here, the repetition of the rinsing operations varies according to the selected mode of the infant clothes-oriented program.

INDUSTRIAL APPLICABILITY

The present invention provides a method for controlling a washing operation of a washing machine, in which washing courses of an infant clothes-oriented program are selected in addition to the selection of washing courses according to kinds of laundry, thereby allowing a user to select one out of various washing courses according to uses of the laundry.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. A method for controlling a washing operation of a washing machine, comprising:
    selecting one of an infant clothes-oriented washing program or a regular washing program based on kinds of laundry to be washed;
    selecting an operating mode from a plurality of operating modes of the infant clothes-oriented washing program when the infant clothes-oriented washing program is selected; and
    performing a washing operation corresponding to the selected operating mode, comprising controlling an operating rate of a motor and a washing temperature of the washing operation based on the selected operating mode of the infant clothes-oriented washing program, wherein selecting an operating mode from a plurality of operating modes of the infant clothes-oriented washing program comprises selecting at least one of a first operating mode that removes protein contaminants from items to be washed, a second operating mode that sterilizes and disinfects items to be washed and prevents damage to the items to be washed, or a third operating mode that increases a sterilizing effect on cotton based items to be washed.

2. The method as set forth in claim 1, wherein performing a washing operation corresponding to the selected operating mode comprising performing a washing operation corresponding to the first operating mode, comprises performing a heated washing course at a temperature of 40° C. for 20 minutes.

3. The method as set forth in claim 1, wherein performing a washing operation corresponding to the selected operating mode comprising performing a washing operation corresponding to the second operating mode, comprises performing a heated washing course that includes controlling the operating rate of the motor so that an ON-time of the motor is shorter than an OFF-time of the motor.

4. The method as set forth in claim 1, wherein performing a washing operation corresponding to the selected operating mode comprising performing a washing operation corresponding to the third operating mode, comprises performing heated washing course without varying the operating rate of the motor.

5. The method as set forth in claim 4, wherein performing the heated washing course without varying the operating rate of the motor comprises performing the heated washing course at a washing temperature of 95° C.

6. The method as set forth in claim 1, further comprising performing a rinsing operation after the washing operation is complete, and repeatedly performing the rinsing operation a predetermined number of times based on the selected operating mode.

* * * * *